United States Patent
Lu et al.

(10) Patent No.: US 7,807,347 B2
(45) Date of Patent: Oct. 5, 2010

(54) IMMUNO-PCR METHOD FOR DETECTING NASOPHARYNGEAL CARCINOMA MARKERS AND KIT THEREOF

(75) Inventors: Hsiang-Yin Lu, Taipei (TW); Tzu-Wei Wang, Taipei (TW); Feng-Huei Lin, Taipei (TW); Pei-Jen Lou, Taipei (TW)

(73) Assignee: National Taiwan University, Taipei (TW)

( * ) Notice: Subject to any disclaimer, the term of this patent is extended or adjusted under 35 U.S.C. 154(b) by 142 days.

(21) Appl. No.: 12/232,763

(22) Filed: Sep. 24, 2008

(65) Prior Publication Data

US 2009/0186336 A1 Jul. 23, 2009

(30) Foreign Application Priority Data

Jan. 21, 2008 (TW) .............................. 97102138 A

(51) Int. Cl.
*C12Q 1/70* (2006.01)
(52) U.S. Cl. .......................................... 435/5
(58) Field of Classification Search ........................ None
See application file for complete search history.

(56) References Cited

OTHER PUBLICATIONS

Piehler et al, Biosensors & Bioelectronics, 2000, vol. 15, pp. 473-481.*
Tsang et al, Head & Neck, 2004, vol. 26(7), pp. 598-602.*
Niemeyer et al,Trends in Biotechnology, 2005, vol. 23, No. 4, pp. 208-216.*

* cited by examiner

*Primary Examiner*—Ali R. Salimi
(74) *Attorney, Agent, or Firm*—Bacon & Thomas PLLC

(57) ABSTRACT

The present invention is related to an immuno-PCR method for detecting nasopharyngeal carcinoma (NPC) and kit thereof, especially related to an immuno-PCR method for detecting markers of early stage NPC and kit thereof. The present invention includes providing a substrate whereon protein markers immobilized; applying a patient's specimen to the substrate; adding a solution which has biotinylated anti-human IgA secondary antibody and incubating the solution; adding a solution with a linker and biotinylated target DNA; proceeding a polymerase chain reaction; and finally, detecting the target DNA fragments via electrophoresis.

1 Claim, 2 Drawing Sheets

| Marker/lane | 1 | 1 | 1 | 1 | 1 | 1 | 1 | 1 | + |
| +serum | 1/1000 | 1/2000 | 1/3000 | 1/4000 | 1/5000 | 1/7500 | 1/1000 | 1/15000 | |

IMMUNO-PCR METHOD FOR DETECTING NASOPHARYNGEAL CARCINOMA MARKERS AND KIT THEREOF

BACKGROUND OF THE INVENTION

1. Field of the Invention

The present invention is related to an immuno-PCR method for detecting nasopharyngeal carcinoma (NPC) and kit thereof, especially related to an immuno-PCR method for detecting markers of early stage NPC and kit thereof.

2. Description of the Prior Art

With the advancement of medical technology and change of living style in modern society, the main cause of death has already been altered from the acute infectious disease to the chronic disease in Taiwan. In addition, according to the statistics of National Health Administration, Executive Yuan, it is known that the cancer is soaring to the first place of top ten major causes of death since 1982, and its mortality rate and incidence have been increased so rapidly with time. It was until the occurrence of cancer symptoms that people start to seek for medical treatment. However, it has almost been the late stage of cancer at this moment, and in most of the case the cancer cells have already been transferred to the whole body. It is then difficult to kill or remove cancer cells completely. Thus, if the cancer can be diagnosed in early stage, there will be much helpful for the treatment and prognosis of patients.

The purpose of cancer screening is to screen the cancer in early stage without symptom by using specific fast and effective tools and methods to achieve early treatment and control as well as to prevent the cancer from deteriorating. The screening should have the following features: high sensitivity, safety and acceptable by the people, etc. The most important one would probably the sensitivity among them, because it can not to be used as the platform for the cancer screening without good sensitivity. All diagnostic tools have their own limitations. For example, the blood serum screening can be used as an index of cancer. However, the screening is not a diagnosis, if the screening result is positive, other physical examinations (functional inspections such as the ultrasonic wave, computer tomography, biopsy etc.) should be conducted for further confirmation.

The nasopharyngeal carcinoma (NPC) is a popular disease in Chinese people, and it is also ranked high in top ten cancers. It is a common cancer found at the head and neck. Once the cancer cells spread and metastasize to other vital organs, it will cause the death of patient. All age levels of people might be affected by this disease, but the peak is for the people at mature stage between 40 and 50 years old. So it can cause serious effect to the patient, patient's family and society. According to the clinical study, it is found that five-year survival rate of early stage nasopharyngeal carcinoma (Phase I, II) (89.7%-75.9%) is much higher than that of later stage (Phase III, IV) (51.3%-22.2%). So, if it can be successfully diagnose in early stage and treated earlier, its prognosis rate can be improved with satisfactory results. However, due to the lack of knowledge for patients in the prevention of nasopharyngeal carcinoma and the early symptom of nasopharyngeal carcinoma is not distinctive as well as the cancer in situ is relatively not distinguishable, the early diagnosis rate of nasopharyngeal carcinoma is still unsatisfactory and a challenge for clinical surgeons.

From anatomy, the nasopharynx lies under the cranium and above the pharynx at the back of the nasal cavity. For sagittal plane, its top is the cranium. Its bottom is the pharynx, oral cavity. For transverse plane, its front is the nasal cavity, paranasal sinus. Its back is the spondyl of neck. For coronal plane, the middle ears are located at its left and right sides. Since the nasopharynx is connected to the lymphatic and lymph node, the malignant expansion and transfer of nasopharyngeal carcinoma will cause the following symptoms. (1) Nose symptom: Including a stuffy nose, thick snivel, stench secretion etc., because the nasal cavity is blocked by the nasopharyngeal tumor or the tumor is festered. (2) Ear symptom: Such as the feeling of ear obliteration, tinnitus, even the emergence of hearing loss. (3) Cervical tumor: It is the initial symptom of more than 70% of the patients. Most patients do not feel pain except for a few patients are infected due to the expansion of lymph node. (4) Headache: It is not the peculiar pain, but a lasting, single-side headache. (5) Neural symptom: The nasopharyngeal carcinoma is occurred at the bottom of cranium. It is very easy to spread to bilateral phranyx and cause the entrapment of trigeminal nerve resulting in the numbness, pain of face, etc. If the spongy sinus is invaded, it will cause the constriction of obducent nerve, and the symptom of diplopia will take place. (6) Others: Such as lockjaw, decrease of physical power, and emaciation etc.

The early symptom of nasopharyngeal carcinoma is not apparent, it is similar to cold, rhinitis, etc., and the symptom is not specific, so it is easy to be neglected. Therefore, most patients are in Phase III or Phase IV of tumor after the nasopharyngeal carcinoma is diagnosed by the doctor. The cancer cells have already been spread to other important organs at this moment, so it is very difficult to be treated, and the mortality rate is extremely high.

The cause of nasopharyngeal carcinoma is still unclear so far, but most research reports indicate that it may have close relationship to the genetic factor, environmental factor, and EB virus infection.

(1) Genetic factor: The occurrence of nasopharyngeal carcinoma has preference in the geography and race. It is comparatively prevailing at the southeast coastal area of China, Taiwan, and Singapore etc. Even the Chinese people immigrated to the American-European area and their descendent have higher incidence of nasopharyngeal carcinoma than the local white people. This reveals the relationship between the nasopharyngeal carcinoma and the genetic factor. It is also found by current research that the type of the human leukocyte antigen (HLA) has the relationship to the emergence of nasopharyngeal carcinoma. If HLA of someone is A2B46DR9, his infection of nasopharyngeal carcinoma will be 2.3 times higher than that of the other people.

(2) Environmental factor: According to the research reported in Hong Kong, it suggests that the emergence of nasopharyngeal carcinoma relates to the fact that Hong Kong people are used to feed children with the salted fish, which contains high dosage of nitrosamine. On the other hand, the epidemiology studies done in Taiwan show that the emergence of the nasopharyngeal carcinoma relates to the working environment, such as poor ventilation, the inclusion of sawdust etc. Researchers also found that heavy smokers have the greater chance to suffer from the nasopharyngeal carcinoma.

(3) EB virus infection: According to the research data of the serology, it is found that a kind of antibody called Epstein-Barr virus (EB, EBV) can be detected in the serum of the nasopharyngeal carcinoma patient, which shows that the patient has been infected by EB virus. And in recent years, the DNA, RNA and EBV protein of EB virus have been proved to be detected in most specimens of nasopharyngeal carcinoma by utilizing of the molecular biology technology. These proteins include the Epstein-Barr virus nuclear antigen 1 (EBNA-1), latent membrane protein 1 (LMP1) and latent membrane protein 2 (LMP2). In addition, some researches data state that the antibody titer is higher in the body of nasopharyngeal carcinoma patient, if the time period is longer than the initial occurrence time of symptom to the time of actual diagnosis. The bigger the tumor is, the higher the antibody titer is. After the radiotherapy, the concentration detected by antibody could be lower down to the level similar to patients without recurrence, but it is still higher than that of the patients with recurrence. So this is further verified that the Epstein-Barr virus has close relationship to the nasopharyngeal carcinoma.

As we know, the nasopharyngeal carcinoma is a kind of malignant tumor in the epithelial tissue of nasopharynx. It is difficult to be diagnosed in early stage, because its position is esoteric. As for 30~50 years old patients, if there are the clinical symptoms of blood snot, stuffy nose, headache, single side tinnitus or deaf, shank lump etc., it should be considered the possibility of the nasopharyngeal carcinoma at first, and carry out necessary biochemical examinations actively. It has many diagnosis methods. The clinical examination methods are described as follows, but each method has its certain degree of disadvantage:

The nasopharyngeal endoscopy: There are two kinds of nasopharyngeal scopes. (1) The regular reflection mirror for the back of nose. The doctor uses a small round mirror to reach the pharynx through the oral cavity to inspect the reflection image of the nasopharynx. Its advantage is rapid and immediate diagnostic without the need of special and expensive apparatus. But there are a lot of disadvantages. The reflection mirror might not be able to stretch into the pharynx due to the vomit reflex of patient or narrow pharynx structure. The image is the reflection image. Its resolution may be relatively poor, and it is unable to determine the minor change. (2) The nasopharyngeal endoscope. It is a kind of expensive fiber endoscope. After local anesthesia, the doctor stretches the mirror to the pharynx through the nose directly, and checks the pathological change of the nasopharynx. Its advantages are high resolution, without loss of minor pathological change, less dead angle, less cause of vomit, and about 5-10 minutes of inspection. The disadvantages are relatively time-consuming and high cost. The nasopharyngeal scope can be used to see local proliferated tubercle or local congestion, festering and ulcer, bleeding, roughness etc. The viable specimen can be biopsied for further histological examination.

The viable tissue biopsy: The vivid tissue inspection shall be carried out for the nasopharyngeal lump and the intumescent lymph node. The biopsy is conducted followed by the tissue morphology analysis of architecture and cytology is conducted by the microscope. When the living tissue is taken for diagnosis, there are some disadvantages: (a) The biopsy belongs to the invasive type medical involvement. It will destroy the tissue structure, and the most serious one might cause other side effects. In addition, the obtained specimens is limited, the variation on the morphology and cytology of tissue will cause the difficulty of diagnosis; (b) Since the distribution of morbid tissues of many diseases are uneven and it lacks of obvious and visible features, so the sampling of tissue is only a random sampling. This kind of tissue sampling by the vision is to cause the obvious sampling error; (c) As for the reading of pathological result, the conclusion might be very different, due to different subjective determination of the pathologist; (d) The completion of pathological diagnosis also needs higher cost and time-consuming, so it is unable to become a kind of real-time diagnostic tool for the standard evaluation of therapy effects of the diseases.

As for the cytology analysis of peeled cell from the nasopharynx: The tissue scratched or by negative pressure is used to obtain samples from the nasopharynx for the investigation of cancer cell. The accurate rate can be up to 70~90%. It is suitable for the screening of early cancer without clear pathological changes. Then the in-viro examination is carried out for the positive and suspicious case. But 60% of the early-stage squamous form of oral cancer attacks the basic membrane to infiltrate into downwards directly, while the top layer of the skin is normal. The negative result is often obtained by the cytology analysis of peeled cell.

X-ray inspection: (1) The X-ray photograph of bilateral nasopharynx and bottom cranium shall be provided for each case. The image of soft tissue is often observed to see the tissue infiltration under the mucous membrane and the destruction condition at the side wall of nasopharynx and bottom cranium. (2) X-ray barium glue radiography. The barium glue is applied into the nasal cavity to inspect the pathological change under the mucous membrane. The image is sharper than that of the nasopharyngeal scope. The smaller the original cancer, the tissue infiltration under the mucous membrane can be found. The X-ray provides the overlaid image of various tissues, and the space resolution and the contrast of every tissue are lower than those of the computer tomography.

The computer tomography (CT): The computer tomography can show the process of small soft tissue near the nasopharynx, help to confirm the direction and position of in-viro inspection, which is beneficial for the diagnosis in early stage. It is beneficial for the confirmation of disease in clinical stage and the determination of treatment methods. The image developer shall be injected for the computer tomography. It may cause disgusting, vomit, and may cause the irritated shock of death in severe condition. In addition, a dosage of radiation is 3-4 times of the chest X-ray, which exceeds the safe dosage of radiation.

The EB virus serology analysis: The cancer cell will secrete some molecules. So it can screen out these molecules from the blood to evaluate the existence of cancer. Only the blood is needed to be drawn for this inspection. There is no side effect, and it is a convenient, fast and comfortable method at present. Traditionally, the indirect fluorescent antibody (IFA) or the enzyme-linked immunosorbent assay (ELISA) is used to detect the IgA antibody (IgA/VCA) of the EB virus shell antigen and the IgA antibody (IgA/EA) concentration of the early antigen. Some literatures show the former one has higher sensitivity but the accuracy is relatively low, while the latter one is totally different. However, the technique of IFA is complicated and time consuming. Every specimen needs to be examined by the physician subjectively under the fluorescence microscope, a significant error might be generated and a large amount of specimens are unable to be screened at the same time. In addition, most of nasopharyngeal carcinoma belongs to the undifferentiated type epidermic cell cancer, the transfer and lymph node metastasis is extremely easy to take place, so the treatment of nasopharyngeal carcinoma is often failed. The lymph node metastasis tends to happen at the late stage of cancer. The current equipment, even more accurate magnetic resonance imaging or positron emission tomography is unable to detect it due to the limited sensitivity. Furthermore, the origin site of nasopharyngeal carcinoma is near the cranium in deep position and other vital organs, there is not easy for operation excising, so the radiotherapy is usually an alternative choice. Once the lymph node metastais, there is no effective treatment at present. If no treatment, the patient can only survive for 4 to 6 months. Even the chemotherapy is applied, the patient can only survive for 12 months. In order to increase the prognosis, it is necessary to develop more sensitive detecting method for early diagnosis. If the treatment is performed immediately when the cancer cell is still confined in the nasopharynx, the outcome of nasopharyngeal carcinoma is quite high at this moment.

Many researches have demonstrated that the nasopharyngeal carcinoma has close relationship to the EB virus. For example, higher EB virus antibody can be detected in the serum of nasopharyngeal carcinoma patient. The molecular biology technology is a good candidate to be used to bind with DNA, RNA and protein of EB virus that can be observed in the tumor cell of nasopharyngeal carcinoma. EB virus gene or protein can be used as the marker for the detection of nasopharyngeal carcinoma. The screening is an important means to diagnose the early stage nasopharyngeal carcinoma, and it should be simple, safe, cheap and acceptable by the public. At present, the marker often used for screening nasopharyngeal carcinoma is EB virus shell antigen antibody IgA (VCA/IgA) and early antigen antibody IgA (EA/IgA). Between them, the VCA/IgA is usually chosen in the enzyme-linked immunosorbent assay. Its sensitivity can be up to about 90%. So, the VCA/IgA can be used as an index of preliminary screening, but its disadvantage is relatively poor with respect to the detection of nasopharyngeal carcinoma. On the contrary, the EA/IgA is better with respect to the nasopharyngeal carcinoma. But its sensitivity is relatively poor, so it is not an ideal candidate for the preliminary screening.

In summary, the current screening methods have different disadvantages. Therefore, it is necessary to develop a more precise detection method to recognize the nasopharyngeal carcinoma in early stage. To sum up, the present invention provides a novel immuno-PCR method for detecting nasopharyngeal carcinoma and kit thereof. The brief illustration of the present invention is described as follows.

SUMMARY OF THE INVENTION

The present invention is related to an immuno-PCR method for detecting nasopharyngeal carcinoma and kit thereof, especially related to an immuno-PCR method for detecting markers of early stage NPC and kit thereof, in order to solve the problem that it is difficult to detect the early stage nasopharyngeal carcinoma clinically. The present invention combines the immune-test method and the polymerase chain reaction to detect the early stage nasopharyngeal carcinoma.

The objective of the present invention is to provide an immuno-PCR method for detecting nasopharyngeal carcinoma and kit thereof, especially related to an immuno-PCR method for detecting markers of early stage NPC and kit thereof. The present invention includes: (1) providing a substrate whereon protein markers are immobilized; (2) applying a patient's specimen to the substrate; (3) adding a solution which has biotinylated anti-human IgA secondary antibody and incubating the solution; (4) adding a solution with a linker and biotinylated target DNA; (5) proceeding a polymerase chain reaction; and finally, (6) detecting the target DNA fragments via electrophoresis.

According to an embodiment of the present invention, the marker of nasopharyngeal carcinoma is a molecule of EB virus.

Preferably, the molecule of EB virus is the Epstein-Barr virus nuclear antigen (EBNA), latent membrane protein (LMP) or early antigen (EA).

More preferably, the molecule of EB virus is the Epstein-Barr virus nuclear antigen 1 (EBNA1).

According to another embodiment of the present invention, the substrate is an organic or inorganic substrate.

According to another embodiment of the present invention, the substrate is a glass substrate.

Preferably, the glass substrate has been modified by a siloxane coupling agent.

More preferably, the siloxane coupling agent is 3-glycidoxypropyltrimethoxysilane (GPTS).

According to another embodiment of the present invention, the human antibody is IgA or IgG.

According to another embodiment of the present invention, the human antibody is IgA.

According to another embodiment of the present invention, the secondary antibody is goat anti-human IgA.

Preferably, the concentration of the secondary antibody is from 0.075 to 0.5 µg/ml.

More preferably, the concentration of the secondary antibody is from 0.075 to 0.25 µg/ml.

According to another embodiment of the present invention, the linker is streptavidin.

Preferably, the concentration of streptavidin is from 1 to 1000 ng/ml.

More preferably, the concentration of streptavidin is 100 ng/ml.

According to another embodiment of the present invention, the concentration of biotinylated target DNA is from 0.001 to 1000 ng/ml.

More preferably, the concentration of biotinylated target DNA is from 0.1 to 1 ng/ml.

Another object of the present invention is to provide a kit of detecting markers of early stage nasopharyngeal carcinoma using the method according to the present invention.

The present invention uses the immune-polymerase chain reaction (Immuno-PCR) as the detecting platform. First, a specific antigen is immobilized on a substrate used as nasopharyngeal carcinoma markers, such as the early antigen (EA), Epstein-Barr virus nuclear antigen (EBNA) or latent membrane protein (LMP). These antigens can catch the corresponding antibodies (anti-EA IgA, anti-EBNA1 IgA or anti-LMP1 IgA) in the serum. Then the anti-DNA complex is added. Finally, PCR is used to amplify DNA fragments and increase signal value to raise the sensitivity.

The basic structure of EB virus includes the nucleus, capsid and envelope membrane. The nucleus includes linear DNA. The capsid is made up of 162 shell particles. The envelope membrane is made up of the nucleus membrane of infection cell. There is the membrane glycoprotein of the virus code on it. It can identify EB virus receptor on the lymphoid cell, and has the function of cell fusion. EB virus is fond of infringing the lymphocyte, especially the B lymphocyte. It can transfer normal B cell to the immortal lymphoblastoid cell lines (LCLs). Except B-cell, EB virus will also infect the epidermic cell and T cell, but the infection route is unclear.

After the host cell is infected by EB virus, the capsid will be peeled off and the linear genome will be released to the cell nucleus. The linear genome will utilize the end repeated sequences to link as cyclic genome. There are two replication methods. One is the latent infection, wherein the viral genome exists as a circular episome and replicates with the cells simultaneously. But the virus only expresses a few viral proteins at this moment, in order to reduce the generation of virons and the crisis of perceiving by the immune system. The other is the lytic infection, wherein the viral genome is reproduced in the form of rolling circle, which is not limited to the cell cycle. A large number of virons are produced and the expression of viral genes is increased greatly at this moment, which leads to the lysis of the infected cells finally.

Most infected cells, including B lymphocytes and nasopharyngeal carcinoma cells, are existed in the latent infection state. The infected cell has the basic genome of EB virus, which can express 11 types of genes, including six kinds of Epstein-Barr virus nuclear antigen (EBNAs): EBNA1, EBNA2, EBNA3, EBNA4, EBNA5 and EBNA6; three types of latent membrane protein (LMPs): LMP1, LMP2A and LMP2B; and two types of RNAs (Epstein-Barr virus-encoded RNAs, EBERs) with small molecule: EBER1 and EBER2. The corresponding antigen and antibody are generated for the EBNA, membrane antigen (MA), virus capsid antigen (VCA), and early protein (EA) of nasopharyngeal carcinoma patients. It has a very important meaning to explain the relationship between the EB virus and nasopharyngeal carcinoma as well as its early diagnosis. According to different expression stage, the antigen of EB virus can be divided into three categories:

(1) Latent phase antigens:

The antigen produced in the latent phase after the cell is infected, which includes the Epstein-Barr virus nuclear antigen (EBNAs) and the latent membrane protein (LMPs). The existence of latent phase antigen can demonstrate the existence of EB virus gene. The latent phase antigen will provide the membrane markers for the killing of T cells.

(2) Early antigens:

The virus protein synthesized before the reproduction of virus nucleic acid is called the early albumen. It is a kind of functional protein, which can inhibit the metabolic process of host cells, and offer the DNA polymerases, RNA polymerases and reverse transcriptases required by the reproduction of viral nucleic acid. The early antigen is not a structural protein of the virus.

(3) Late antigens:

The late antigen is a structural protein of the virus, which is the structural protein of capsid and envelope membrane. The late antigens exist in the cells wherein virus replicates, and they are in a large amount.

There are two kinds of potential carcinogenic proteins synthesized by EB virus in the infected cell, one is Latent phase protein 1 (LMP1), and the other one is the Epstein-Barr virus nuclear antigen 1 (EBNA1). According to current research, it is found that both proteins can influence the normal function of the cell. The cell will become cancer cell, and the amount will be increased. Clinically, the above-mentioned two kinds of proteins can be detected in the tissue of most nasopharyngeal carcinoma patients.

The present invention combines the immune-test method and polymerase chain reaction to detect the early stage nasopharyngeal carcinoma. The present invention provides an immuno-PCR method for detecting nasopharyngeal carcinoma markers. The immune-polymerase chain reaction method is used as the detecting platform. As for the main scheme, a specific antigen is immobilized on a substrate used as the nasopharyngeal carcinoma marker, such as the early antigen (EA), Epstein-Barr virus nuclear antigen (EBNA) or latent membrane protein (LMP). These antigens can catch the corresponding antibodies (anti-EA IgA, anti-EBNA1 IgA or anti-LMP1 IgA) in the serum of patient. Then the secondary anti-DNA complex is added. The present invention uses the goat anti-human IgA as the biotinylated secondary antibody. Finally, PCR is used to amplify DNA fragments and increase signal value to raise the sensitivity. It can be used as the tool for the diagnosis of nasopharyngeal carcinoma and the tracing of heal in the future.

DESCRIPTION OF THE PREFERRED EMBODIMENT

Figure 1:
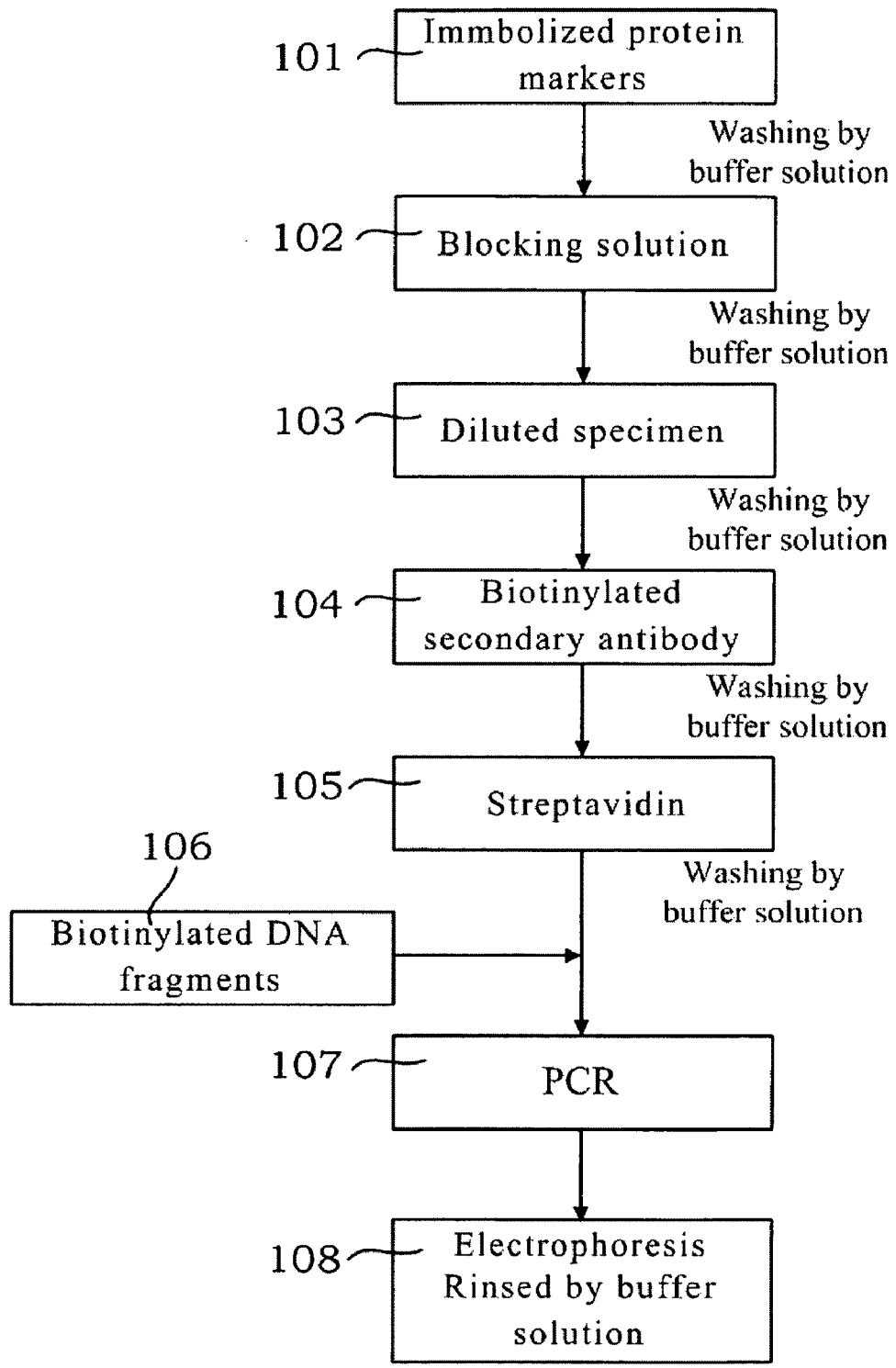
FIG. 1 shows the flow chart of the immuno-PCR method for detecting nasopharyngeal carcinoma of the present invention.

The present invention provides an immuno-PCR method for detecting nasopharyngeal carcinoma. The present invention will be understood sufficiently by the description of the following embodiment, and those skilled in the art can finish it accordingly. But the enforcement of this invention shall not limited by the following embodiment.

Embodiment 1: Activation and Modification of Substrate Surface

Because the stability of protein is relatively poor, it is difficult to maintain its biochemical activity for a long time, and it is apt to be influenced by the experiment condition (solvent type, temperature, pH value etc.) and cause the change or modification of protein structure and the loss of activity. Therefore it is necessary to carry on the chemical modification of substrate or add the extra additive, in order to maintain the structure and biochemical activity of protein. According to the characteristics of substrate and immobilized molecules, suitable immobilization method can be selected. Its basic steps are: (a) The activation of substrate: the specific functional group is produced on the substrate surface after chemical modification. The functional group can bind the protein. (b) The immobilization of protein: the protein can be bound to the activated substrate through the functional groups (eg., amino group, carboxyl group) of amino acids itself.

The substrate suitable for the present invention includes an organic or inorganic substrate, so long as its surface can immobilize active biological molecule. The solid substrate used in this embodiment is glass. Its advantage is that the glass surface has no permeating feature. Thus, it only needs a small amount of sample. The glass surface does not have proper chemical activation site, such as the functional groups of —OH, —NH2, —COOH etc., the immobilization rate will be reduced due to low chemical activity of functional groups. As for the inert glass, it can react with the siloxane reagent to generate various kinds of functional groups on the surface. The siloxane used in this embodiment is 3-glycidoxypropyltrime thoxysilane (GPTS), which carries an epoxy group at one end. Compare to the silane with other functional group, the glass modified by the silane with epoxy group has better property. It has high sensitivity, good signal-background ratio and easy to be prepared. In addition, its surface not only can react to the amino group but also can react to other functional group with affinity, because it has high reactive epoxy group.

After the glass substrate (such as the glass bead) is washed in the alcohol, it is soaked in the piranha solution (70% H2SO4, 30% H2O2) for surface activation (1 hour of reaction). Then the substrate is washed in the ultrasonic wave for 15 minutes, and rinsed by the deionized water. Finally, it is blown dry by nitrogen.

The 3-glycidoxypropyltrimethoxysilane (GPTS) is dissolved in toluene solution to form 2.5% of GPTS solution.

The glass substrate is placed in GPTS solution to react at 60° C. for 4 hours. After the reaction is completed, it is washed three times by 95% alcohol, and then dried overnight. The substrate is further put in the oven for the cross-linking reaction.

The modified glass substrate can be checked by water contact angle, atomic force microscope and X-ray photoelectron spectroscopy to confirm whether the modification of glass substrate is successful or not. The surface of glass substrate modified by the siloxane will have larger water contact angle, because there is a layer of organic molecules on the surface. The polarity of its hydrocarbon chain and epoxy group is smaller than hydroxyl group, so the contact angle is larger for the water droplet on the surface.

Embodiment 2: Immobilization of Markers

Please refer to FIG. 1, which is the schematic flow diagram of the present invention. As shown in Step 101, 50 μL of EBNA1 (10 μg/mL) is added on the modified glass substrate, and reacted at 37° C. for 4 hours. The buffer solution (10 mM Tris, pH 7.3, 150 mM NaCl) is used to wash out un-reacted antigens and impurities. Then according to Step 102, the blocking solution (10 mM Tris/HCl, pH 7.6, 6% skimmed milk power, 0.2% NaN3, 0.05% Tween-20 and 5 mM EDTA) is added. After reacting at 37° C. for 1 hour, the glass substrate is rinsed by the buffer solution.

Embodiment 3: Immuno-Binding Reaction

Refer to Step 103 in FIG. 1, the diluted serum is added to be tested. It is reacted at 37° C. for 1 hour. The specific antibody in the serum is combined with the antigen immobilized on the substrate surface to form the solid phase antigen-antibody complex. After it is washed by the buffer solution, only the specific antibody is left on the substrate, and other compositions in the serum will be washed out. Then 50 μl of biotinylated antibody (0.25 μg/ml of concentration) is added, and reacted at 37° C. for 1 hour (Step 104).

After washing by the buffer solution again, the streptavidin (100 ng/ml) is added and incubated at the room temperature for 30 minutes (as shown in Step 105). As shown in Step 106, after washing, biotinylated DNA fragments (1 ng/ml) is added, and reacted at 37° C. for 1 hour. After it is washed completely, the amount of biotinylated DNA fragments will be proportional to the amount of antibody to be tested in the sample.

Embodiment 4: Polymerase Chain Reaction

According to the biotinylated DNA fragments used in this embodiment, the primer pairs with sequences of SEQ ID NO: 1 and SEQ ID NO: 2 are added. After it is amplified by PCR reaction, DNA fragments with 235 base-pairs will be obtained. 50 μl of 50 mM KCl (dissolved in 10 mM Tris/HCl, pH 8.3, 1 mM Mg2+), 50 μM of dNTP solution (PCR Master Mix, GeneMark), 50 pmole of each primer pairs are added, and prepared glass beads into PCR test tube. After the mixture is mixed, the PCR test tube is then put into PCR Thermocycler (Corbett Life Science, Australia) for PCR reaction (Step 107). PCR reaction is set at 95° C. and 5-minute denaturing. Then 30 cycles are carried out at 94° C., 30-second denaturing, 55° C., 30-second annealing, 72° C., 30-second extension. It is reacted at 72° C. for 15 minutes, then the temperature is reduced to 4° C.

Figure 2A:
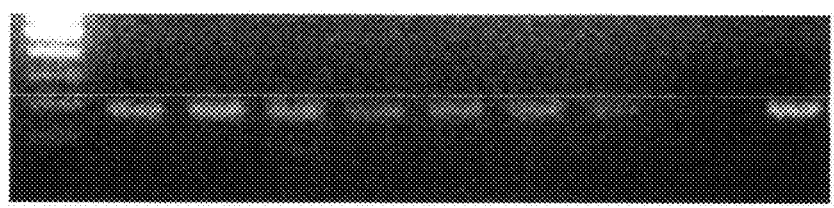
FIG. 2 shows the electrophoresis results for different nasopharyngeal carcinoma patients of a preferred embodiment of the present invention.
Figure 2B:
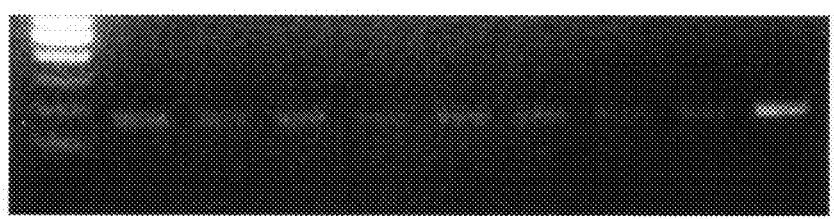
Figure 2C:
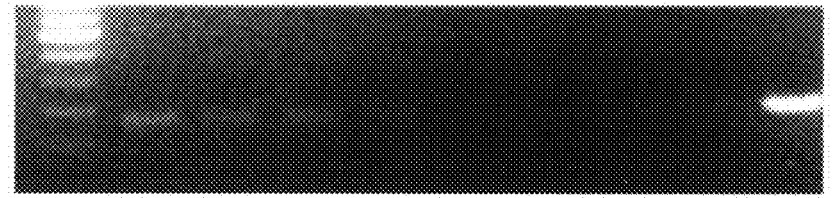

After the reaction is completed, QIAGEN Gel/PCR DNA Fragments Extraction Kit (Qiagen, USA) is used to purify the product of DNA fragments, which is then stored at −20° C. 10 μl of product is dropped out with a pipet to take out for electrophoresis in 1.5% agar with ethidium bromide (Step 108). DNA and deionized water are added into PCR mixture for the reaction, to be used as positive and negative control groups. The results are shown in FIG. 2.

In order to compare the detecting range of the method of present invention and the traditional immune-detecting method, the serum to be tested is diluted serially, to assess the detecting ability of the method of present invention. Generally speaking, when the conventional immuno-enzyme method is used, if the serum is diluted to 2,000 folds, the difference of absorption value between the nasopharyngeal carcinoma patient and normal human is hard to be distinguished. FIG. 2 shows the detecting results for the serial dilution of NPC patients' serum by the method of present invention. The result shows that after the serum is diluted to 1,000 folds, there is signal generated. As for some patients, even the serum is diluted to 15,000 folds, the signal is still generated. The difference between the normal person and patient can be compared obviously. It is known that the method of present invention has higher sensitivity compared to the traditional immune-detecting method.

It is understood that various other modifications will be apparent to and can be readily made by those skilled in the art without departing from the scope and spirit of this invention. Accordingly, it is not intended that the scope of the claims appended here to be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. An immuno-PCR method for detecting a molecule of Epstein-Barr Virus Nuclear Antigen 1 (EBNA1) of early-stage nasopharyngeal carcinoma marks, comprising steps of:

providing a modified 3-glycidoxypropyltrimethoxysilane (GPTS) glass substrate whereon 50 μL of EBNA1 (10 μg/mL) been immobilized and reacted at 37° for 4 hours;

adding a blocking solution having 10 mM Tris/HCl, pH 7.6, 6% skimmed milk power, 0.2% NaN3, 0.05% Tween-20 and 5 mM EDTA, and reacting at 37° for 1 hour;

adding a diluted serum and reacting at 37° for 1 hour;

adding 50 μL of goat anti-human IgA (0.25 μg/ml of concentration) and reacting at 37° for 1 hour;

adding streptavidin (100 ng/ml) and incubating at a room temperature for 30 minutes;

adding biotinylated DNA fragments (1 ng/ml) and reacting at 37° for 1 hour;

adding a primer pairs with sequences of SEQ ID NO: 1 and SEQ ID NO: 2 for proceeding a polymerase chain reaction; and detecting a target DNA fragments via a electrophoresis method in order to detect the molecule of Epstein-Barr Virus Nuclear Antigen 1 (EBNA1) of early-stage nasopharyngeal carcinoma marks.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
agctcgcggt gggcatcgac                    20

<210> SEQ ID NO 2
<211> LENGTH: 20
<212> TYPE: DNA

-continued

```
<213> ORGANISM: Artificial Sequence
<220> FEATURE:
<223> OTHER INFORMATION: Primer

<400> SEQUENCE: 2
ttcagggccg cctggctctt                                          20
```